United States Patent [19]

Kung

[11] Patent Number: 5,240,487

[45] Date of Patent: Aug. 31, 1993

[54] WARM AIR REGISTER FILTER AND SCENT DISPENSER

[75] Inventor: Kirk Kung, Vancouver, Canada

[73] Assignee: Metro-Pacific Holdings (Canada) Inc., Vancouver, Canada

[21] Appl. No.: 961,010

[22] Filed: Oct. 14, 1992

[51] Int. Cl.$^5$ ............................................. A61L 9/12
[52] U.S. Cl. ...................................... 55/486; 55/492; 55/500; 55/501; 55/509; 55/DIG. 31; 55/DIG. 35; 422/123
[58] Field of Search ................. 55/486, 492, 500, 501, 55/507, 509, 511, DIG. 31, DIG. 35, 279, 527, 357, 482; 239/60, 56; 422/124, 123; 428/905; 261/99, 107, DIG. 17, DIG. 65; 454/289-291, 247, 328, 337; D23/366

[56] References Cited

U.S. PATENT DOCUMENTS

| | | | |
|---|---|---|---|
| 1,737,532 | 11/1929 | Allen | 55/279 |
| 1,854,569 | 4/1932 | Welch | 55/DIG. 31 |
| 1,886,460 | 11/1932 | Andersen | 55/DIG. 35 |
| 2,493,257 | 1/1950 | Malme | 55/492 |
| 2,557,279 | 6/1951 | Greenberg | 55/DIG. 31 |
| 3,019,127 | 1/1962 | Czevwonka et al. | 55/316 |
| 3,040,501 | 6/1962 | Pietsch | 55/509 |
| 3,494,113 | 2/1970 | Kinney | 55/486 |
| 4,047,914 | 9/1977 | Hansen et al. | 55/492 |
| 4,065,262 | 12/1977 | Petroff | 55/279 |

Primary Examiner—Richard L. Chiesa
Attorney, Agent, or Firm—Shlesinger, Arkwright & Garvey

[57] ABSTRACT

A frame carries a variable flow scent dispenser and supports an air filter. The frame, dispenser and filter are to be inserted as a unit into a forced air heating and/or cooling system duct adjacent to the duct outlet through a floor or wall register. The filter is in the form of a two-ply fibrous sheet with an opening between the plies to receive the frame and dispenser. The filter collects dirt particles borne by the warm air as it leaves the duct and is quickly and easily replaceable. The scent dispenser is a container for scented air freshening material and has apertures through opposite walls, which walls are disposed transversely to the direction of airflow, permitting warm airflow through the container. The warm air will cause evaporation from the scented material and will entrain the vaporous scent and disperse the scent throughout the room. A slide is adjustable to increase or decrease the aggregate area of the apertures in one of the apertured container walls so that the intensity of the air freshening scent carried into the room can be controlled.

12 Claims, 2 Drawing Sheets

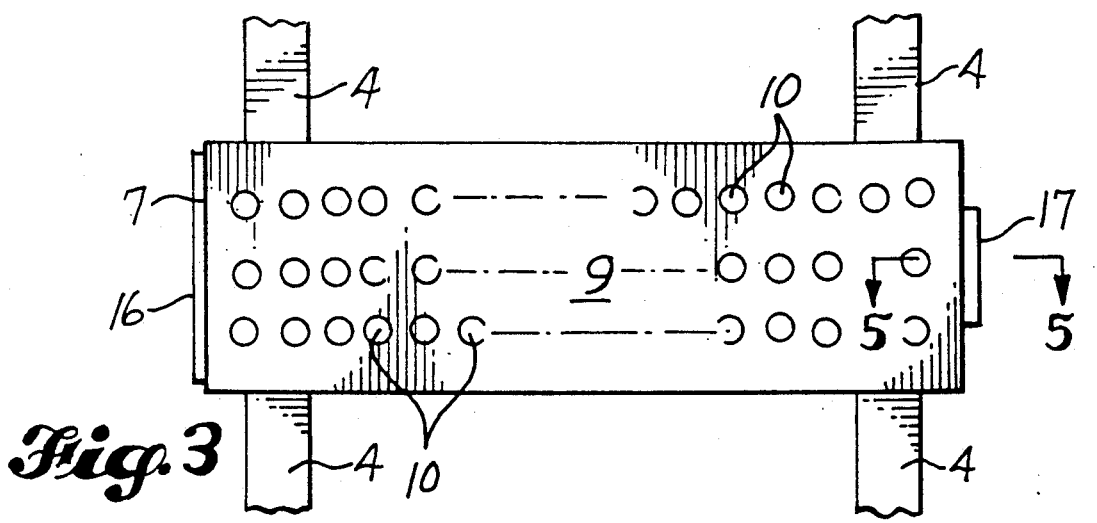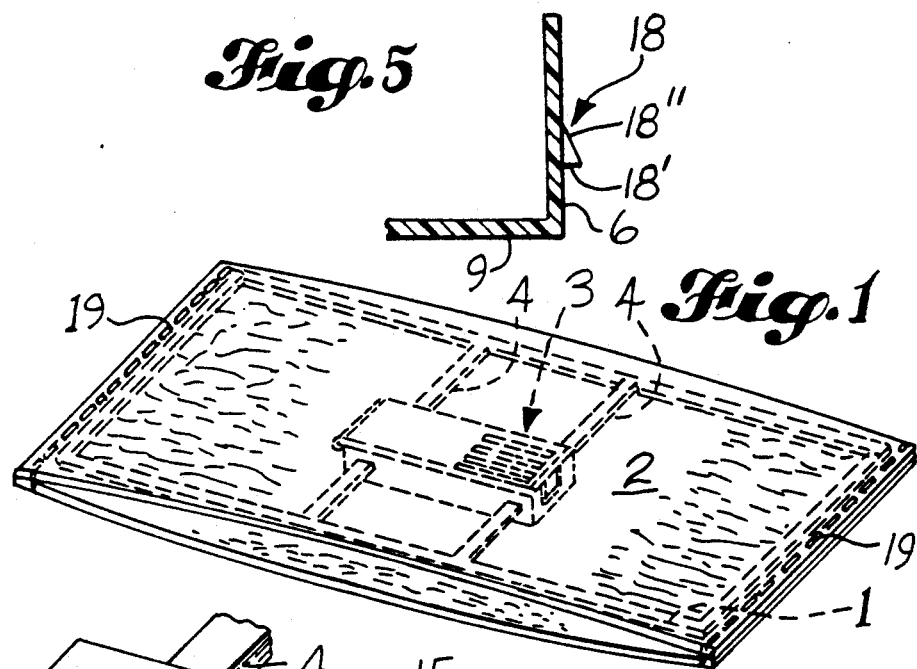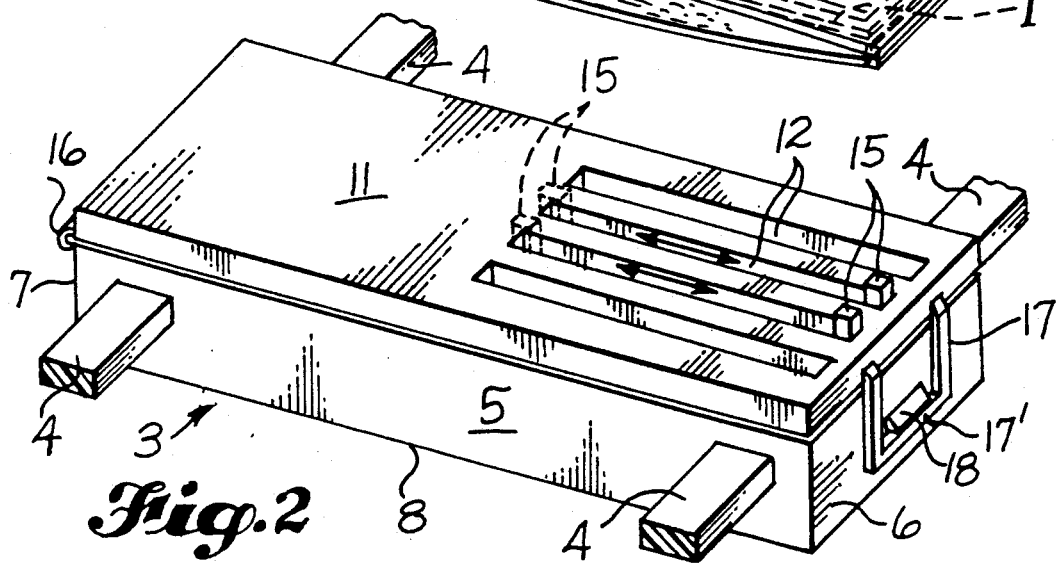

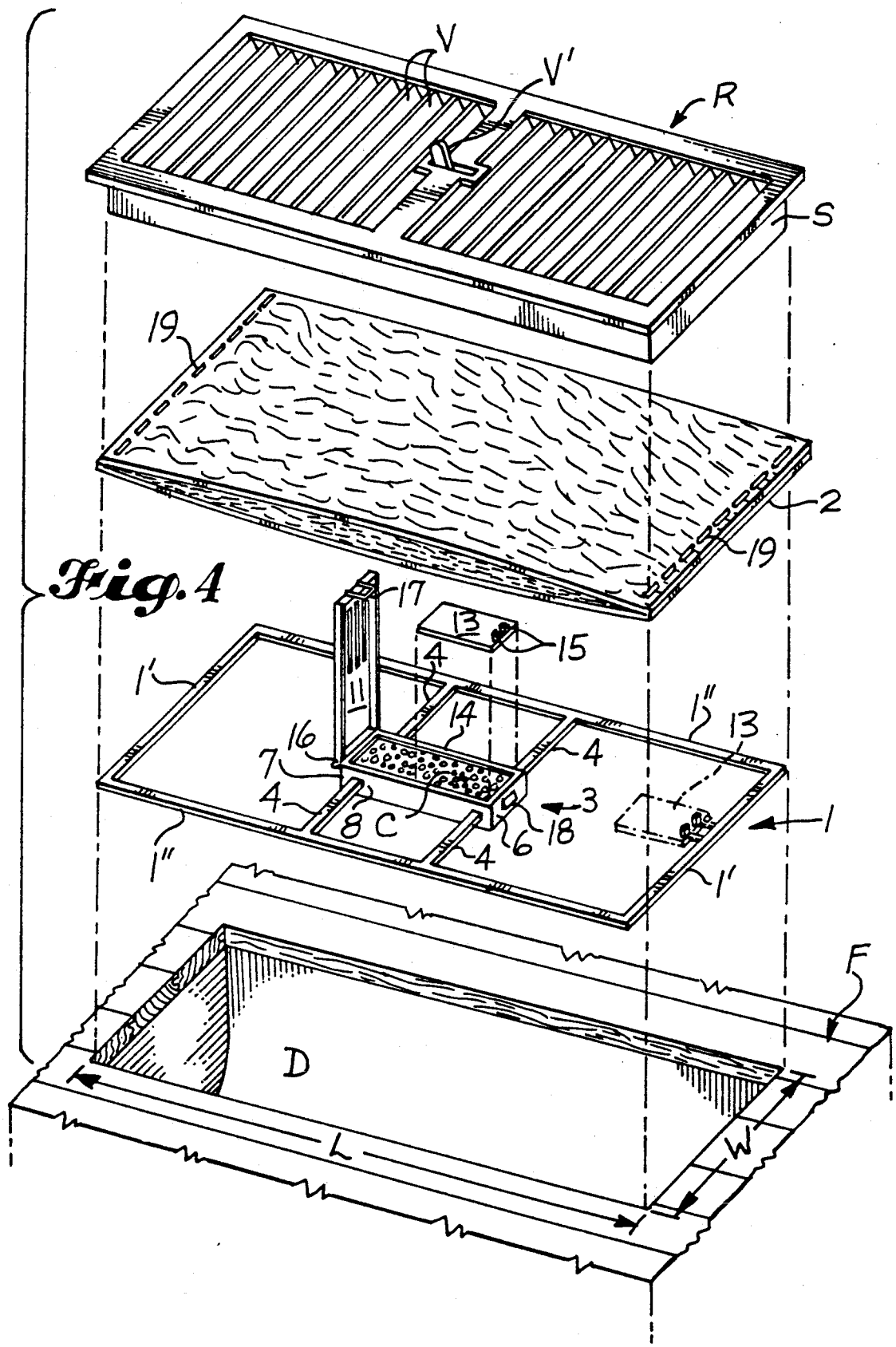

WARM AIR REGISTER FILTER AND SCENT DISPENSER

SUMMARY OF THE INVENTION

The invention is a filter unit for a forced air duct outlet in heating and/or cooling systems, the principal components of which are a resilient substantially planar frame which can be inserted in the outlet of a forced air duct and a disposable filter having two substantially planar plies of fibrous sheet material forming a sleeve open at one side and having a size and shape similar to and somewhat larger than the frame so that the frame will be completely encased within the filter sleeve. The frame has a size and shape substantially conforming with the internal wall of a duct outlet so that, when the frame is inserted into and disposed transversely of the duct outlet, it will press the filter sleeve margin into substantially continuous engagement with the internal wall of the outlet duct. The frame includes at least one transverse rib which serves as a grip that assists in the placement of the filter carrying frame into the duct outlet and carries a scented material receiving container.

The container includes apertured inlet and outlet walls permitting flow of air from the duct through the volatile scented material so that such airflow will vaporize some of the scented material and carry it into the room being cooled or heated by the airflow. The apertured walls are disposed substantially parallel to the plane of the frame so that the apertures are disposed substantially perpendicular to such plane and so that the air entering and exiting from the container maintains its normal direction of airflow.

The container includes a slidable cover adjacent to one of the apertured walls and tracks for guiding the cover between selected positions whereby the apertures in such wall are fully closed, partially closed, or substantially fully opened for controlling the flow of air through the container and scent-carrying material therein.

It is preferred that the scent-carrying material is in the form of scented pellets, that the frame is comprised of molded polypropylene and that the filter sleeve is comprised of nonwoven polyester fiber sheet material. If it is desired that cigarette smoke, for example, be prevented from escaping from the duct, the filter material may be impregnated with appropriate materials, such as activated carbon.

OBJECTS OF THE INVENTION

It is an object of the invention to provide supplemental filters for the duct outlets of a forced air heating system effective to reduce substantially the amount of soot and dirt transmitted from a warm air register into the room.

Another important object of the invention is to provide a filter system by means of which consumers can select different filter materials to fit individual needs such as pollen and/or odor reduction and to fit the type of heating system used in the individual's home or apartment.

It is a further object to provide a supplemental filter which can be changed quickly and easily while minimizing the amount of dust and dirt which can escape the filter during replacement.

Another object of the invention is to utilize the natural warm air stream efficiently to disperse air freshening scent throughout the room.

A further object of the invention is to provide an air freshening system which can be readily controlled as to type of scent and as to the intensity of a particular type of scent within a room.

It is also an object to provide disposable filters impregnated with particular materials, such as activated carbon, to remove selected particles or odors, such as cigarette smoke, from the air being transmitted by the forced air duct.

BRIEF DESCRIPTION OF THE DRAWINGS

FIG. 1 is a top perspective of a warm air filter and scent dispensing unit according to the invention.

FIG. 2 is a top front perspective of the scent container and intensity control device.

FIG. 3 is a bottom plan of the scent container shown in FIG. 2.

FIG. 4 is an exploded view of the frame and scent container, scent intensity control slide and filter installed in a warm air duct behind a floor register.

FIG. 5 is a fragmentary cross section taken on line 5—5 of FIG. 3 showing the cover latch tongue of the preferred form of the invention.

PRIOR ART

Removal of dirt particles from furnace heated air is conventionally accomplished by means of a filter placed between the duct carrying cooled air back to the furnace and the fan compartment of the furnace. The filtered cool air then passes through the heat exchanger and is heated thereby. The heated air then is channeled through the hot air duct system and into the rooms to be heated. Such conventional filters are effective to a greater or lesser degree depending on the type of fuel burned by the furnace and on the frequency of filter replacement. Especially in the case of oil-fired furnaces, a substantial amount of dirt remains in the heating system, which is evidenced by sooty deposits on walls and floors surrounding the warm air room registers.

Passive air fresheners using liquid, semisolid or pellet-like scented substances or potpourri intended to be dispersed in the rooms in which they are placed are well known. They may be in the form of scented candles, decorative containers, or heatable cups to be set on furniture or hung from walls, for example. Dispersal of the scent is limited and is generally confined to a relatively small area around the device itself. Usually the intensity of the scent adjacent to the device cannot be controlled, or control is very limited. Furthermore, in order for the scent to be dispersed to remote areas of the room, the intensity of the scent adjacent to the device is often objectionable. Even if a scent container is hung on a wall above a warm air register, only a small portion of moving air from the register is likely to pass through the container and dispersal of the scent is limited.

DETAILED DESCRIPTION OF THE PREFERRED EMBODIMENT

As shown best in FIGS. 1 and 4, the filter and scent dispenser unit has a rectangular frame 1 that supports a filter sleeve 2 and a scent dispenser 3 supported by a pair of spaced transverse ribs 4. The frame ends 1' are slightly shorter than the standard width W of an opening through a wall or floor F and the frame sides 1" are slightly longer than the standard length L of such opening.

Filter 2 preferably is made from nonwoven polyester sheet material which is closed along one side and both ends. The filter 2, as shown in FIGS. 1 and 4, is made from a single sheet folded along one side and sewn together at the two ends, as indicated by stitching 19. The ends of the filter sleeve alternatively may be heat sealed. Filter 2 is mounted on the frame by fitting the frame into the open side of the filter sleeve and sliding the frame and sleeve relatively in transversely opposite directions. The filter 2 should be slightly wider than the frame 1 so that the filter will completely cover the outlet end of duct D and entrap substantially all of the particulate material borne by the warm air emerging from the duct outlet.

When a filter sleeve 2 has been fitted over frame 1 and the unit is to be inserted in the outlet of duct D, the register R is lifted from the opening and set aside. One end 1' of the frame will be inserted into the duct outlet and pressed against the duct wall by an installer holding the opposite end 1' of the frame by the thumb and forefinger of one hand. The leading end 1' will be butted against the duct D wall at a location spaced from the surface of floor F approximately equal to the depth of the register skirt S. The installer will grasp container 3 or ribs 4, through the filter material, with the thumb and forefinger of the other hand so that the container 3 and ribs 4 may be lifted while the trailing frame end 1' is pressed downward to cause the frame sides 1" to flex, thereby decreasing the distance between frame ends 1' to permit the entire frame to be inserted into the duct outlet. When the frame and container are released, the sides 1" will spring back to more nearly linear disposition, thereby securing the unit in the duct outlet with a friction fit. If the frame, as so inserted into the duct opening, is spaced from the surface of floor F a distance less than the depth of register skirt S, when the register R is placed over the floor opening, the skirt extend into the outlet, press against the frame 1 and move the frame further along the duct wall until the register is flush with the floor.

Floor registers are typically equipped with movable vanes V which can be opened or closed with a lever V' to control the volume of airflow into the room. Conventionally the skirt S is of a depth that will provide adequate space to permit lever V' and vanes V to be moved without interference. Although the function of the register skirt has been to assure that the floor opening is adequate and to assure that the edges of carpeting or flooring material are forced out of any interference with operation of the vanes, such skirt also cooperates with applicant's filter unit so simplify its installation. Therefore, any adult occupant of a house or apartment may readily install applicant's device and may change filters as necessary without special skill or tools.

Replacement filters are small, flexible and light so they can be easily stored. The unit can be removed as easily as it is installed. The unit is small enough that it can be inserted into a bag, wastebasket or garbage can and the dirty filter sleeve slipped off of the frame without tugging or shaking so that the dirt stays in the filter and is not broadcast into the air.

The frame can be made of flexible metal wire, but it is preferred that the frame be made of a rigid but resilient plastic such as polypropylene. Such plastic construction provides assurance that the frame will not absorb and retain heat and, therefore, can be removed at any convenient time without any risk that a person will experience any sensation of being burned. Furthermore, the frame and scent dispenser can be molded as a single unit which substantially reduces the cost of manufacture and the price to the consumer.

The scent dispenser 3 includes a rectangular tray 5 with upright end walls 6 and 7 and side walls 8. As shown in FIG. 3, the tray bottom 9 has a plurality of apertures 10. The number, size, shape and arrangement of such apertures are not critical so long as the rigidity of the tray bottom is not undermined and the scented material, shown in the form of pellets or crystals C, is unable to fall through the apertures. For purposes of illustration, perforations 10 are shown as three parallel rows, lengthwise of the tray, of circular apertures, the axes of which are perpendicular to the plane of the tray bottom and aligned with the current of air passing from duct D through vanes V of register R.

Tray 5 receives scent pellets C that are retained in the tray by cover 11. Lengthwise slots 12 in cover 11 allow heated air entering the dispenser through perforations 10 in the tray bottom 9 to pass out of the dispenser with scent vapor entrained in such airflow. The room freshening scent is carried by the warm air current and thus is positively dispersed through the room with much greater uniformity of intensity than in prior art dispensers.

Dispenser 3 is supported on transverse ribs 4 of frame 1. Although tray 5 could be fabricated separately and mounted in a frame by bonding tray bottom 10 to the upper surface of ribs which extend from side to side of the frame, for example, it is preferred that the frame and tray be molded as a single unit with ribs 4 extending from opposite frame sides 1" into tray side walls 8 without passing through such side walls or through the interior of the tray. With such construction, there are no transverse ribs to interfere with the flow of heated air through bottom apertures 10 over the scent pellets C and out through slots 12.

A slide 13 is supported on tracks 14 formed in the inner and upper margins of tray side walls 8 for sliding lengthwise of tray 5 beneath cover slots 12, as indicated by the arrows in FIG. 2 Two posts 15 carried near one end of the upper slide surface project through two of slots 12 so that the slide can be manipulated when the tray is closed by cover 11. Slots 12 are shown as four parallel slots extending from one end of cover 11 for a distance slightly less than half the length of the cover. Slide 13 is of a length slightly greater than half the length of the cover and tracks 14 extend the full length of the tray interior. The slide can be moved lengthwise of tray 5 and cover 11, by finger engagement of the free ends of posts 15, between a position in which slots 12 are sealed from communication with the interior of the tray and a position in which slots 12 are in full communication with such interior. The thickness of cover 13 is slightly greater than the depth of tracks 14 to assure that slide 13 is in substantially continuous engagement with the cover interior creating a friction fit to maintain the slide in any selected position with respect to the length of slots 12 to control the intensity of scent released from the tray.

If a frame is packaged, shipped and stored prior to use with scent material contained in the tray, the slide would be set to fully closed position, with posts 15 in the solid line position shown in FIG. 2. To achieve maximum intensity of scent when the frame is inserted into a warm air duct, as described above, posts 15 would be moved to the left position shown in broken lines in FIG. 2. A homeowner or an apartment tenant can adjust the slide and thereby control the scent intensity in accordance with his or her personal preferences. If a guest temporarily occupying a room in which a scent dispenser of the instant invention has been installed is allergic to o otherwise bothered by the particular scent in use, the dispenser can be easily closed, and the room will soon be purged of the scent by the circulation of unscented air from the register.

Although cover 11 is made separately and snapped into place on the tray, it is preferred that the cover also be molded as part of the frame and tray. In the preferred form of the fabrication of the invention, cover 11 is integrally connected to tray end wall 7 by a hinge 16. As noted above, the frame and dispenser preferably are made of a rigid, resilient plastic material, such as polypropylene. Therefore, it is preferred that latch yoke 17 have a substantially rectangular configuration with a substantially horizontal cross bar 17' and that latch tongue 18 be of substantially triangular cross section, as shown in FIG. 5. The lower leg or latching edge 18' of the latch tongue is substantially perpendicular to tray end wall 6 and the outer leg of the triangle is disposed at acute angles with the outer end of leg 18' and with end wall 6 to form a latch ramp 18". When the tray cover is to be opened, a fingernail is slipped behind the yoke bar 17' until it is lifted outwardly and upwardly to engage ramp 18', whereupon the resilience of the yoke will urge bar 17' upwardly and inwardly along ramp 18" and the resilience of hinge 16 will urge the cover upward into open position.

In the preferred form of the invention described above and shown in the drawings, the frame, tray and cover are molded as a single unit. Preferably slide 13 is molded together with the frame and attached to the frame by two thin links, as shown in broken lines at the right of FIG. 4, so that slide 13 can be readily snapped off the frame and put into the tray by either the manufacturer or the consumer.

Scented material, in the form of pellets C, semisolid blocks or liquid contained in a scent-permeable sac or in the form of potpourri, for example, may be sold with the frame, but preferably is sold separately so that the purchaser can follow individual preferences in scent selection as well as purchase scent material in sufficient quantity to refill the dispenser from time to time. The preferred scent material is in pellet form and is sold under the trademark Aroma Techetts, manufactured by Aroma Tech of Matawan, N.J.

Frame 1 can be quickly and easily removed from and installed in a typical warm air duct outlet for refilling dispenser 3 and/or replacing filter 2.

The filter and scent dispenser of the present invention has been described in connection with a forced air heating system duct and register typically found in living units. The present invention may be used in forced air heating and/or cooling system whether in residential, commercial or industrial settings. The invention has the greatest utility in applications where forced air duct outlets are of moderate size and are readily accessible by means of an easily removed register, grill or other duct cover. In air conditioning installations, because evaporation of the scented material will occur more slowly in a cool airstream, the slide should be in the fully open position shown by the broken-line position of posts 15 in FIG. 2.

Filters 2 of the present invention may be provided with different characteristics depending on the normal room occupant's particular needs. It is often unrecognized that most of the particulate material carried by the warm air stream originates from any and all rooms served by a forced air heating system because such particulate material is gathered from the rooms, entrained in the system through the cold air returns and mixed in the furnace. Filters having different characteristics may be provided. For example, the filter sheets may be made with finer polyester fibers and/or greater density of fibers per cubic unit to adapt to the type of heating fuel. Such variations in filter material can be provided to trap pollens and other small particles to relieve allergy sufferers. The filters can include activated carbon to reduce odors such as cigarette smoke or cooking odors.

I claim:

1. A filter unit for forced air duct outlet in ventilation systems, comprising:
   a) a substantially planar frame means for placing within an air duct outlet;
   b) filter means including an opening for removably receiving said frame means, said filter means comprises first and second substantially planar plies of fibrous sheet material connected to each other only at the side end portions thereof so as to form a sleeve open at both ends thereof to form said opening;
   c) container means for receiving scent-carrying means, said container means being positioned substantially parallel to the plane of said frame means;
   d) said frame means including rib means for supporting said container means, said rib means including at least one rib member extending generally transversely to said frame means; and
   e) said container means including aperture means for directing passage of air from a forced air source through said container means.

2. The filter unit defined in claim 1, wherein:
   a) said rib means includes a pair of rib members extending generally transversely to said frame means.

3. The filter unit defined in claim 1, wherein:
   a) said rib means is located substantially equidistantly from the opposite end portions of said frame means.

4. The filter unit defined in claim 1, wherein:
   a) said container means includes a pivotable cover means for gaining access thereto.

5. The filter unit defined in claim 1, wherein:
   a) said container means includes adjusting means for controlling the flow of air through said container means.

6. The filter unit defined in claim 1, wherein:
   a) said aperture means comprises a plurality of generally elongated slots on one side of said container means.

7. A filter unit for a forced air duct outlet in heating and/or cooling systems, comprising:
   a) resilient substantially planar frame means;
   b) disposable filter means having two substantially planar plies of fibrous sheet material of a shape similar to and a size slightly larger than said frame means;
   c) a substantial portion of the margin of said plies being connected together to form sleeve means having a marginal opening of an extent sufficient for passage of said frame means into said sleeve means;

d) said frame means having a size and shape in conformity with the internal wall of a duct outlet such that said frame means, upon insertion into and disposition transversely of the duct outlet, will press the filter means margin into substantially continuous engagement with said duct outlet internal wall;

e) said frame means including transverse rib means located substantially equidistantly from opposite end portions of said frame means for strengthening said frame means and forming grasp means for flexing said frame means during insertion of the filter unit into a forced air duct outlet; and f) container means carried by the rib means for receiving volatile scent-carrying means, said container means having a pair of spaced substantially parallel walls disposed substantially parallel to the plane of the frame means, and aperture means through each of said walls, said aperture means are substantially perpendicular to the plane of said frame for directing passage of air from a forced air duct through said container means and said scent-carrying means.

8. The filter unit defined in claim 7, in which the container means includes slidable cover means adjacent to one of the container means apertured walls and track means for guiding said cover means between selected positions whereby the apertures in said wall are fully closed, partially closed, or substantially fully opened for controlling the flow of air from a duct through the container means and scent-carrying means therein.

9. The filter unit defined in claim 7, in which the scent-carrying means are scented pellets.

10. The filter unit defined in claim 7, in which the frame means comprises molded polypropylene.

11. The filter unit defined in claim 7, in which the filter means comprises nonwoven polyester fiber sheet material.

12. The filter unit defined in claim 7, in which the filter means includes activated carbon.

* * * * *